(12) United States Patent
Akashi et al.

(10) Patent No.: US 6,395,037 B1
(45) Date of Patent: May 28, 2002

(54) HYDROXYAPATITE, COMPOSITE, PROCESSES FOR PRODUCING THESE, AND USE OF THESE

(75) Inventors: Mitsuru Akashi, Kagoshima; Tetsushi Taguchi, Tsukuba; Akio Kishida, Suita; Akio Hayashi, Tokyo, all of (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 09/462,220

(22) PCT Filed: Aug. 4, 1998

(86) PCT No.: PCT/JP98/03461

§ 371 (c)(1),
(2), (4) Date: Jan. 3, 2000

(87) PCT Pub. No.: WO99/58447

PCT Pub. Date: Nov. 18, 1999

(30) Foreign Application Priority Data

May 8, 1998 (JP) .......................... 10-126083

(51) Int. Cl.[7] .................................................. A61F 2/36
(52) U.S. Cl. ...................... 623/23.56; 423/308; 423/311
(58) Field of Search ............................ 623/23.51, 23.53, 623/23.56, 23.61, 23.62, 23.63, 423

(56) References Cited

U.S. PATENT DOCUMENTS

| | | | | |
|---|---|---|---|---|
| 4,606,912 A | * | 8/1986 | Rudy et al. .................... 424/52 |
| 4,871,384 A | * | 10/1989 | Kasuga ......................... 65/30.1 |
| 5,071,434 A | * | 12/1991 | Tsuzuki et al. ................ 623/16 |
| 5,472,734 A | | 12/1995 | Perrotta et al. ................. 427/2 |
| 5,651,884 A | * | 7/1997 | Ichitsuka et al. .......... 210/198.2 |
| 5,858,318 A | * | 1/1999 | Luo ............................ 423/308 |
| 5,990,381 A | * | 11/1999 | Nishihara ..................... 623/11 |
| 6,159,449 A | * | 12/2000 | Winston et al. ............... 424/52 |
| 6,214,368 B1 | * | 4/2001 | Lee et al. .................... 424/423 |

FOREIGN PATENT DOCUMENTS

| | | |
|---|---|---|
| JP | 09-020508 | 1/1997 |
| JP | 09-040408 | 2/1997 |
| JP | 09-255317 | 9/1997 |

* cited by examiner

Primary Examiner—David J. Isabella
Assistant Examiner—Urmi Chattopadhyay
(74) Attorney, Agent, or Firm—Darby & Darby (57) ABSTRACT

A hydroxyapatite consisting substantially of $Ca_{10}(PO_4)_6(OH)_2$, and having a crystal structure which has at least two diffraction peaks at 31–32 degrees and 26 degrees in X-ray diffractometry; and a process for producing a hydroxyapatite which comprises the step (A) of immersing a substrate in a first aqueous solution containing calcium ions and a second solution containing $PO_4$ ions to generate the hydroxyapatite at least on the surface of the substrate and the step (B) of recovering the hydroxyapatite from the substrate.

4 Claims, 11 Drawing Sheets

HYDROXYAPATITE, COMPOSITE, PROCESSES FOR PRODUCING THESE, AND USE OF THESE

FIELD OF ART

The present invention relates to a novel hydroxyapatite that resembles a constituent of bones and can be used for various tissues such as artificial bones and medical materials, a complex having this hydroxyapatite, and a production method thereof. The present invention also relates to use of the hydroxyapatite or the complex in the manufacture of an artificial tissue and a medical material, utilizing the hydroxyapatite or the complex.

BACKGROUND OF ART

Main layers of tissues such as a bone and a tooth consist of inorganic solid substances that resemble hydroxyapatite (sometimes abbreviated hereinbelow as HAp). It is known that ceramic materials having biocompatibility can be used for fixing damaged bones and teeth. Known examples of such materials include "Bioglass" (trade name, manufactured by Nippon Electric Glass Co. Ltd., Otsu. Siga. Japan, containing $Na_2O$—$CaO$—$SiO_2$—$PiO_5$), which is used mainly as a restorative material in dental surgery, a sintered compact of HAp ($Ca_{10}(PO_4)_6(OH)_2$) that is used mainly as a bone filling material, and a crystallized glass containing apatite and wollastonite ($CaO$—$SiO_2$) (trade name "Cerabone A-W", manufactured by Nippon Electric Glass Co. Ltd., Otsu. Siga. Japan) which is used for an artificial otoconite or an ilium spacer.

There have been made attempts to cover a surface of a material having high strength such as a metal with these ceramic materials for producing a bone substitute. Further, there has been developed a so-called biomimetic process, that is, a method for forming a HAp layer on a surface of various organic high molecular materials that can readily be processed, for application to production of artificial tissues other than bones that has flexibility and durability.

This biomimetic process is performed as follows: introducing glass particles containing as principal constituents $CaO$ and $SiO_2$ into an aqueous solution having the same ion concentration as that of human body fluid (simulated body fluid); immersing an organic high molecular material therein to have many apatite cores formed on the surface of the organic high molecular material; taking the organic high molecular material out of the simulated body fluid; and immersing the organic high molecular material in a solution having 1.5 times the ion concentration of the simulated body fluid. It is reported that, by this biomimetic process, the apatite cores grow naturally on the organic high molecular material to form a desired thickness of a bone-like HAp layer that is compact and homogeneous (J. Biomed.Mater.Res. vol.29, p349–357(1995)).

However, the rate of generation of HAp in this biomimetic process is so slow that even the long reaction time, such as more than two weeks, is not sufficient for obtaining the organic high molecular material having the HAp thereon that can be used as an artificial bone.

The aforementioned ceramic materials are required to have biocompatibility such that the materials can bind to live bones. Researches as to composition and configuration have been made to obtain such biocompatibility. Recently, it has been found out that the crystal structure of the ceramic materials is as important as the composition and the configuration thereof for improving biocompatibility. For example, it is known that the crystal structure of a human bone shows specific diffraction peaks shown in FIG. 10 in X-ray diffractometry (Biomaterials, 11, p568–572, 1990).

However, HAp having a crystal structure that resembles such a structure of the human bone is not hitherto known. For example, although the HAp obtained by the aforementioned biomimetic process is reported to be a bone-like HAp layer, it does not have such a crystal structure.

DISCLOSURE OF THE INVENTION

The first object of the present invention is to provide a novel hydroxyapatite having the composition and the crystal structure that resemble those of bones and exhibiting an excellent biocompatibility, and a production method thereof.

The second object of the present invention is to provide a method for producing a hydroxyapatite that can produce a hydroxyapatite having the composition and the crystal structure that resemble those of bones and exhibiting an excellent biocompatibility, in an extremely high production rate and efficiency.

The third object of the present invention is to provide a complex that has a hydroxyapatite having excellent biocompatibility and a bone-like crystal structure, and that is useful as a medical material, an artificial bone and various artificial tissues other than bones that are required to have flexibility, as well as a production method of such a complex.

The fourth object of the present invention is to provide a method for producing a complex by which a hydroxyapatite having excellent biocompatibility and a bone-like crystal structure can be produced in an extremely high rate and efficiency, and by which a complex useful as a medical material, an artificial bone and various artificial tissues other than bones that are required to have flexibility can readily be obtained.

The fifth object of the present invention is to provide a tissue such as an artificial bone having a hydroxyapatite that has the composition and the crystal structure which resemble these of bones, and that has excellent biocompatibility.

In developing a biocompatible material for an artificial bone and various tissues having flexibility and durability, the present inventors made extensive researches for production method of a novel hydroxyapatite that resembles inorganic solid substances constituting bones not only in the composition but also in the crystal structure. As a result, the present inventors found out that a novel hydroxyapatite which resembles bones in the crystal structure as well as the composition can be produced by alternately immersing a substrate such as an organic high molecular polymer or various metals in a solution containing calcium ions and substantially free of phosphate ions, and in another solution containing phosphate ions and substantially free of calcium ions, to complete the present invention.

That is, according to the present invention, there is provided a hydroxyapatite consisting essentially of $Ca_{10}(PO_4)_6(OH)_2$, and having a crystal structure that causes diffraction peaks at 31–32° and 26° in X-ray diffractometry (referred to hereinafter as "HAp of the present invention").

According to the present invention, there is also provided a method for producing the hydroxyapatite comprising the steps of (A) immersing a substrate in a first aqueous solution which contains calcium ions and is substantially free of phosphate ions and in a second solution which contains phosphate ions and is substantially free of calcium ions, to produce the HAp of the present invention at least on a surface of the substrate; and (B) recovering the HAp of the present invention from the substrate.

According to the present invention, there is further provided a complex having the HAp of the present invention at least on a surface of a substrate.

According to the present invention, there is further provided a method for producing the complex comprising the step of (A) immersing a substrate in a first aqueous solution which contains calcium ions and is substantially free of phosphate ions and a second solution which contains phosphate ions and is substantially free of calcium ions, to produce the HAp of the present invention at least on a surface of the substrate.

According to the present invention, there is further provided an artificial tissue consisting essentially of the HAp of the present invention or the complex.

According to the present invention, there is further provided use of the HAp of the present invention or the complex in the manufacture of a medical material.

BRIEF DESCRIPTION OF THE DRAWINGS

FIG. 5 is a set of microscopic photographs of cross-sections of the PVA gel showing the formation of HAp of the present invention on and/or in the PVA gel. (a) is a photograph of the cross-section of the PVA gel after immersing the gel alternately in the calcium chloride solution and in the sodium hydrogenphosphate solution one time each, (b) is a photograph of the cross-section of the PVA gel after immersing the gel alternately in the calcium chloride solution and in the sodium hydrogenphosphate solution five times each, (c) is a photograph of the cross-section of the PVA gel after immersing the gel alternately in the calcium chloride solution and in the sodium hydrogenphosphate solution ten times each, and (d) is a photograph of the cross-section of the PVA gel after immersing the gel alternately in the calcium chloride solution and in the sodium hydrogenphosphate solution fifteen times each.

PREFERRED EMBODIMENTS OF THE INVENTION

The composition of the HAp of the present invention is substantially $Ca_{10}(PO_4)_6(OH)_2$. The present HAp has a crystal structure that causes diffraction peaks at least at 31–32° and 26° in X-ray diffractometry, which peaks are specific for those of the crystal structure of human bones. As the apparatus for observing the X-ray diffraction, "Geigerflex 2013" (trade name, a product of Rigaku Co.,Tokyo, Japan) may be used. The X-ray diffraction may be performed with $CuK\alpha/30$ kv/15 mA X-ray at the scan speed of 2°/min.

The HAp of the present invention that substantially has a composition of $Ca_{10}(PO_4)_6(OH)_2$ may further contain impurities that inevitably enter during, e.g., production steps. The HAp of the present invention that substantially has composition $Ca_{10}(PO_4)_6(OH)_2$ may also contain apatite carbonate and/or apatite which partially lacks Ca due to affection of carbonate ions that exist in the solutions for the production. The crystal structure of the present HAp may further cause peaks other than the aforementioned specific diffraction peaks in X-ray diffractometry, as long as it resembles that of human bones.

The HAp of the present invention may be produced by two essential steps that are (A) immersing a substrate in a specific first aqueous solution and another specific second solution to form HAp of the present invention at least on the surface of the substrate, and (B) recovering the HAp of the present invention from the substrate.

The specific first aqueous solution for the step (A) contains calcium ions and is substantially free of phosphate ions. Since existence of the phosphate ions is liable to decrease the rate of HAp generation, the first aqueous solution usually contains the calcium ions and is completely free of the phosphate ions. Examples of the first aqueous solution may include a calcium chloride aqueous solution, a calcium acetate aqueous solution, a tris-buffered calcium chloride solution, a tris-buffered calcium acetate solution, and mixtures thereof.

Considering rate and efficiency of HAp generation, the calcium ions concentration of the first aqueous solution may preferably be 0.01 to 10 mol/l, and more preferably 0.1 to 1 mol/l. When the first aqueous solution is a tris-buffered solution, pH thereof may preferably be 6 to 10, and more preferably 7.4, but not limited thereto.

The specific second aqueous solution for the step (A) contains phosphate ions and is substantially free of calcium ions. Since existence of the calcium ions is liable to decrease the rate of HAp generation, the second aqueous solution usually contains the phosphate ions and is completely free of the calcium ions. Examples of the second aqueous solution may include a sodium hydrogenphosphate aqueous solution, an aqueous solution of sodium dihydrogenphosphate or ammonium dihydrogenphosphate, a tris-buffered sodium hydrogenphosphate solution, a tris-buffered solution of sodium hydrogenphosphate or ammonium dihydrogenphosphate, and mixtures thereof.

Considering rate and efficiency of HAp generation, the phosphate ion concentration of the second aqueous solution may preferably be 0.01 to 10 mol/l, and more preferably 0.1 to 1 mol/l. When the second aqueous solution is a tris-buffered solution, pH thereof may preferably be 6 to 10, and more preferably 7.4, but not limited thereto.

Examples of the combinations of the first aqueous solution and the second aqueous solution may include a combination of the calcium chloride aqueous solution and the sodium hydrogenphosphate solution, and a combination of the calcium acetate aqueous solution and the solution of sodium dihydrogenphosphate or ammonium dihydrogenphosphate, but not limited thereto.

The first aqueous solution and the second aqueous solution may further contain other ions as long as these ions are not harmful for achieving the object of the present invention. Existence of 2.5 mM or more of magnesium ions ($Mg^{2+}$) is not preferable since it possibly forms tricalcium phosphate (TCP).

The substrate for the step (A) is not particularly limited as long as it is not soluble in the first and the second aqueous solutions. Examples of the substrate may include an organic high molecular polymer, various metals, and various ceramics.

The organic high molecular polymer may be polyurethane, polyethylene, polypropylene, polyester, nylon, polycarbonate, Teflon, or a silicone elastomer. The molecular weight of the organic high molecular polymers is not particularly limited. The configuration thereof is not particularly limited either, but may preferably be in the form of plate, film, membrane, cylinder, mesh or fiber.

Examples of a particularly preferable organic high molecular polymer may include a hydrophilic cross-linked high molecular polymer that turns into a gel form upon contacting with an aqueous solution. Employment of the hydrophilic cross-linked high molecular polymer enables formation of the HAp of the present invention not only on the substrate but also inside of the substrate. In addition, this also enables easy formation of the resulting HAp of the present invention in a desired shape.

Although cross-linking degree of the hydrophilic cross-linked high molecular polymer is not particularly limited, the polymer may preferably be a hydrogel material that swells in the first and the second aqueous solutions to gelate. In order to increase production efficiency of the present HAp, it is preferable to employ a hydrogel material having high swelling ratio. Examples of such material may include hydrogel materials mainly made of synthetic or natural organic polymers such as polyvinyl alcohol, polyethylene glycol, poly-γ-glutamic acid, collagen, glucosylethyl methacrylate (GEMA), a partially sulfated GEMA, mucopolysaccharide (such as hyaluronic acid), and fibronectin, and copolymers having units of these polymers. Particularly, a partially cross-linked hydrophilic resin that can give hydrogel is preferable. Specific examples thereof may include a cross-linked polyvinyl alcohol, polyacrylamide, polyethylene agarose, and collagen. The cross-linked polyvinyl alcohol may be produced by partially cross-linking the polyvinyl alcohol with a difunctional aldehyde such as glutaraldehyde.

Examples of the various metals may include stainless, titanium, platinum, tantalum, cobalt, chromium, molybdenum, and alloys of two or more of these metals; and sol-gel products containing titanium such as a titania gel.

In the step (A), the substrate may be immersed in the first aqueous solution and in the second aqueous solution in accordance with methods such as (1) performing once or more cycles of operation of immersing the substrate in the first aqueous solution followed by immersing the substrate in the second aqueous solution, and (2) performing one or more cycles of operation of immersing the substrate in the second aqueous solution followed by immersing the substrate in the first aqueous solution. By repeating the cycles, an increased amount of the HAp of the present invention may be obtained. The number of cycles may usually be 2 to 20 times, and preferably 5 to 10 times. In the case of repeating the cycles according to the aforementioned method (1), the final immersion does not have to be in the second aqueous solution, but may be in the first aqueous solution. Similarly, in the case of repeating the operation according to the aforementioned method (2), the final immersion does not have to be in the first aqueous solution, but may be in the second aqueous solution.

The duration for immersing the substrate in the first aqueous solution may suitably be selected considering the rate and efficiency of the HAp generation. The total immersion time may usually be 10 minutes to 7 days, preferably 30 minutes to 3 days, and more preferably 1 hour to 24 hours. The duration for immersing the substrate in the second aqueous solution may also suitably be selected considering the rate and efficiency of the HAp generation. The total immersion time may usually be 10 minutes to 7 days, preferably 30 minutes to 3 days, and more preferably 1 hour to 24 hours. When the immersing cycles of the substrate in the first and second solutions are repeated, the duration for each immersion may suitably be selected considering the aforementioned preferable total immersion time.

Temperature of the aqueous solutions upon immersing the substrate in the solutions may suitably be selected considering the rate and efficiency of the HAp generation, and may usually be 0 to 90° C., and preferably 4 to 80° C.

By the above step (A), the HAp of the present invention may be formed at least on the surface of the substrate. By selecting the material and configuration of the substrate, the HAp of the present invention may be formed not only on the substrate but also inside of the substrate. On the surface of the substrate, the HAp of the present invention may usually be formed as a layer. A complex of the HAp of the present invention and the substrate obtained by the step (A) may be used as the complex, artificial tissue and medical material of the present invention which will be discussed later.

For preparing the HAp of the present invention, step (B) is subsequently performed for recovering the HAp of the present invention from the substrate.

The method for recovering is not particularly limited as long as it can separate the HAp of the present invention. For example, when the organic high molecular polymer is employed as the substrate, the HAp of the present invention may be recovered by baking the complex of the present HAp and the substrate produced in the aforementioned step (A) at a high temperature, preferably 600° C. or more, to burn and remove the organic high molecular polymer.

The obtained HAp of the present invention as it is may be used for producing various medical materials. Alternatively, the HAp may be processed into a desirable shape or may be subjected to various known baking treatments or surface treatments to obtain various medical materials.

The complex of the present invention has the HAp of the present invention at least on the surface thereof, and, depending on the sort and shape of the substrate, may also have the HAp inside of the substrate. The HAp of the present invention formed on the substrate is usually in a form of a layer. The thickness of the layer may suitably be selected in accordance with the sort and configuration of the substrate, and the use of the complex. For example, the thickness of the HAp layer of the present invention on the complex is preferably about 0.0001 to 5 mm. The complex may be formed in various shapes by suitably selecting the shape of the substrate, or by processing the complex into a desired shape.

The complex of the present invention may thus be utilized as various artificial tissues such as an artificial bone, by suitably selecting the sort or shape of the substrate, or by processing the complex into a desired shape. For example, employment as the substrate of an organic high molecular polymer having flexibility such as a hydrogel material results in a complex having elasticity, capability of maintaining the shape like a cartilage and excellent biocompatibility of the present HAp. Such a complex exhibits good adhesion with muscles, high elasticity and high durability against twisting in an organism, and can therefore be used as various artificial tissues that cannot be produced with prior art ceramic materials.

The complex of the present invention maybe prepared by, e.g., the aforementioned step (A). Preferable examples of the substrate therefor may include the aforementioned examples of the substrate. Depending on the use of the complex, suitable one may be selected among the examples. After the step (A), the step of processing into a desired shape or the step of baking or surface treatment that are publicly known may be performed.

Since the HAp of the present invention resembles bones in both composition and crystal structure, it is useful as various tissues such as an artificial bone.

EXAMPLES OF THE INVENTION

The present invention will be explained more in detail with reference to the following Synthesis Examples, Examples and Comparative Examples. However, the present invention is not limited thereto.

Analysis and measurement in Examples were performed as follows:
(1) X-ray diffractometry was performed with "Geigerflex 2013" (manufactured by Rigaku Co., Tokyo, Japan) and CuKα/30 kv/15 mA X-ray at the scan speed of 2°/min.
(2) Swelling ratio of hydrogels ($SR_1(\%)$) was measured at 25° C. by immersing the cross-linked high molecular polymer in each aqueous solution for a predetermined time to form a cross-linked gel, wiping the residual water off the surface of the gel, and weighing the gel. The swelling ratio was calculated according to the following equation:

$$(SR_1(\%)) = ((W - W_0)/W_0) \times 100$$

In the equation, $SR_1$ stands for the swelling ratio of the hydrogel, $W_0$ stands for the weight of the sample substrate before treatment, and W stands for the weight of the sample substrate after water absorption.
(3) The amount of HAp formation on the cross-linked polymer PVA gel was calculated according to the following equation:

Amount of HAp formation=(dry weight of complex of PVA and HAp)−(dry weight of PVA)=(dry weight of the complex of PVA and HAp)−(wet weight of PVA)/(1+$SR_2$)

In the equation, $SR_2$ stands for ($SR_1/100$).

Synthesis Example 1

To a 10 wt % aqueous solution of PVA having average polymerization degree of 2000 and saponification ratio of 99.5% (manufactured by Wako Pure Chemical Industries, Ltd.), a predetermined concentration of glutaraldehyde (manufactured by Nakarai Chemical Co., the concentration for cross-linking was varied in the range of 0.2 to 3 mol %) and 1N HCl (manufactured by Wako Pure Chemical Industries, Ltd.) were added. The mixture was left stand for 2 days to synthesize 4 sorts of PVA gels having a thickness of 1 mm. Each resulting PVA gel was swelled in water for 3 days. The swelling ratio of each gel was determined to be 4.1, 10.4, 16.8 and 30.1. After washing these gels, discs having a diameter of 1 cm were stamped out from these gels, which were used as sample substrates in the following Examples.

Comparative Example 1

Formation of HAp by Biomimetic Process 30 ml of a simulated body fluid having a similar ion concentration to that of a human plasma (SBF: $Na^+$142 mM, $K^+$5.0 mM, $Mg^{2+}$1.5 mM, $Ca^{2+}$2.5 mM, $Cl^-$148 mM, $HCO_3^-$4.2 mM, $HPO_4^{2-}$1.0 mM, $SO_4^{2-}$0.5 mM) was mixed with bioactive glass ($CaO$—$SiO_2$) (glass G) particles. 100 mg of the gel material disc made of a PVA gel (cross-linking agent concentration 1 mol %, swelling ratio 18) was immersed in the mixture for 2 days. Temperature of the simulated body fluid during immersion was maintained at 36.5° C.

The immersed PVA gel was further immersed in 30 ml of another simulated body fluid having 1.5 times the ion concentration of the aforementioned simulated body fluid, for 8 days. Temperature of the simulated body fluid during immersion was maintained at 36.5° C., and this simulated body fluid was exchanged once in two days. After finishing immersion, the PVA gel was washed with distilled water, and dried at room temperature. The result of X-ray diffraction analysis of the resulting HAp is shown in FIG. 9.

Figure 3:
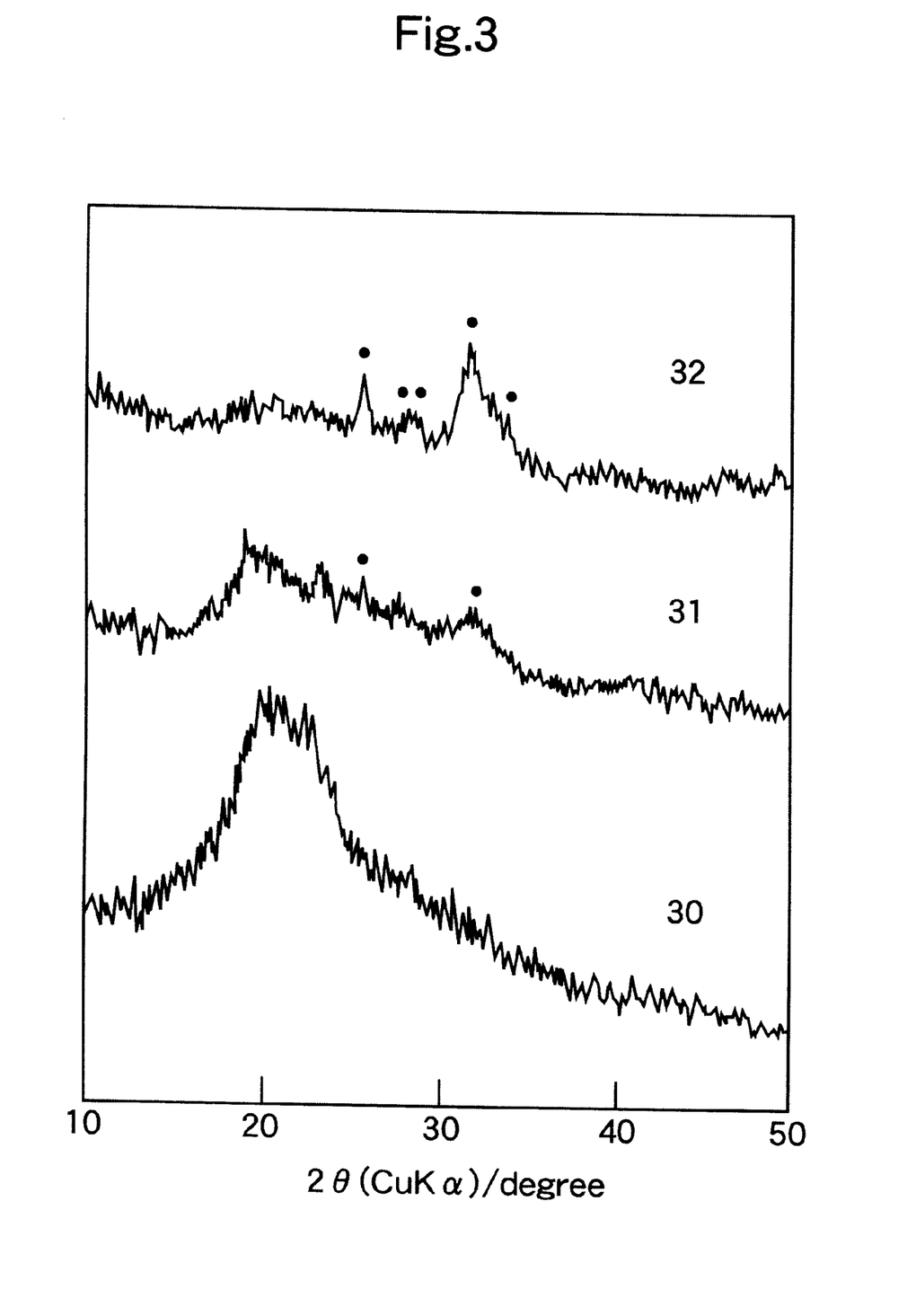
FIG. 3 is a chart showing the X-ray diffraction of a PVA gel having swelling ratio of 10.4, the X-ray diffraction of the PVA gel after immersing the gel alternately in the calcium chloride solution and in the sodium hydrogenphosphate solution one time each, and the X-ray diffraction of the PVA gel after immersing the gel alternately in the calcium chloride solution and in the sodium hydrogenphosphate solution five times each.
Figure 9:
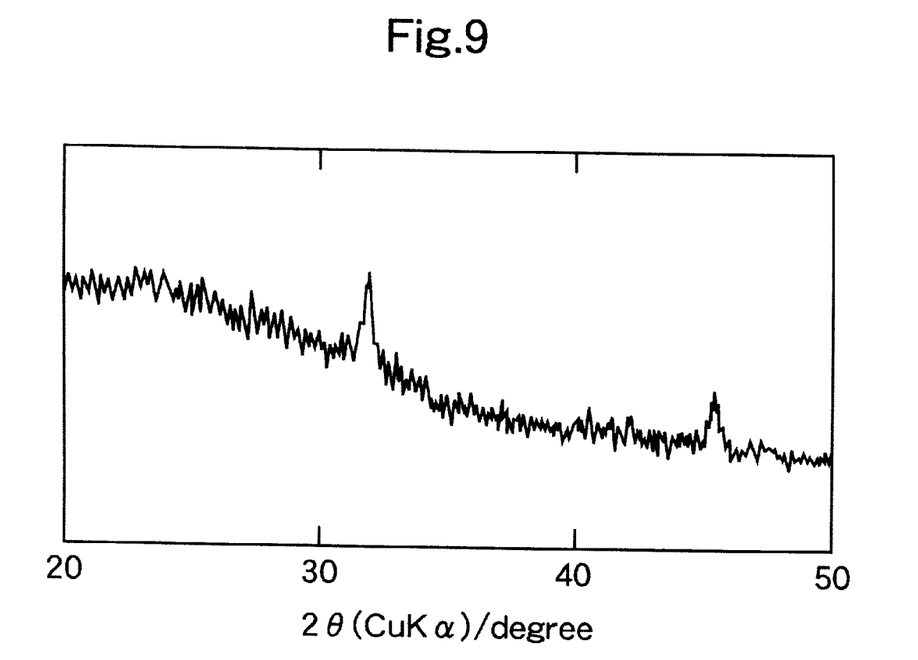
FIG. 9 is a chart showing the result of X-ray diffraction for the crystal structure of HAp formed by the biomimetic process in Comparative Example 1.
Figure 10:
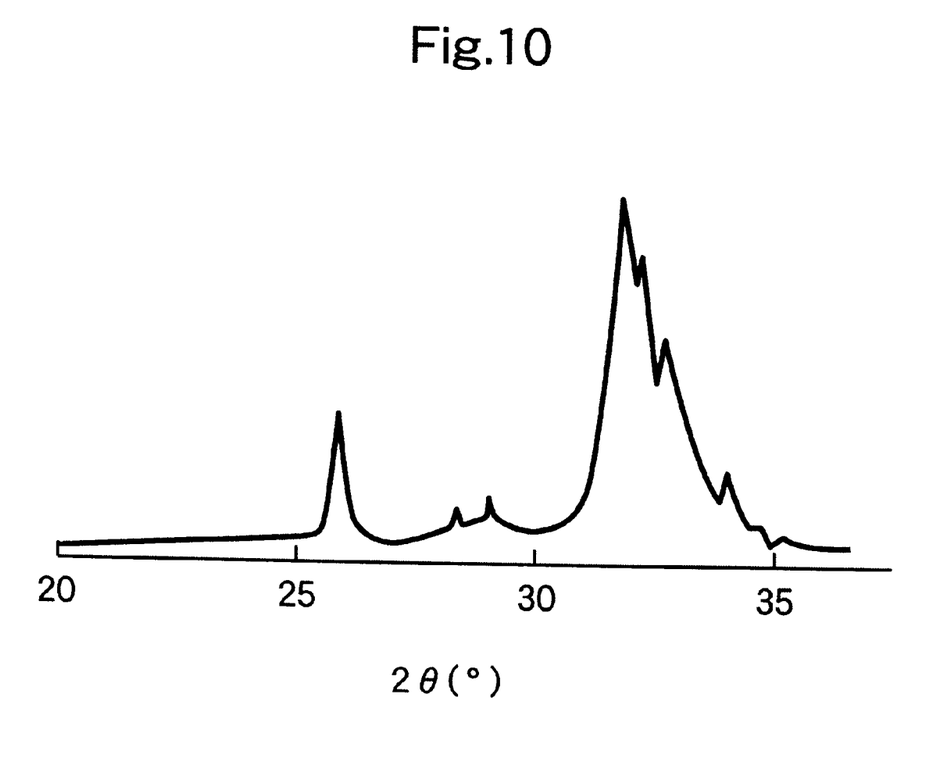
FIG. 10 is a chart showing the result of X-ray diffraction for the crystal structure of a human bone.

From the result in FIG. 9, it is seen t hat the HAp formed by the biomimetic process has a different crystal structure from that of the present HAp shown in FIG. 3 and that of a human bone shown in FIG. 10.

In the above biomimetic process, the amount of HAp produced in 24 hours of reaction at 37° C. after formation of cores was measured and found out to be about 0.08 mg.

Example 1

Figure 1:
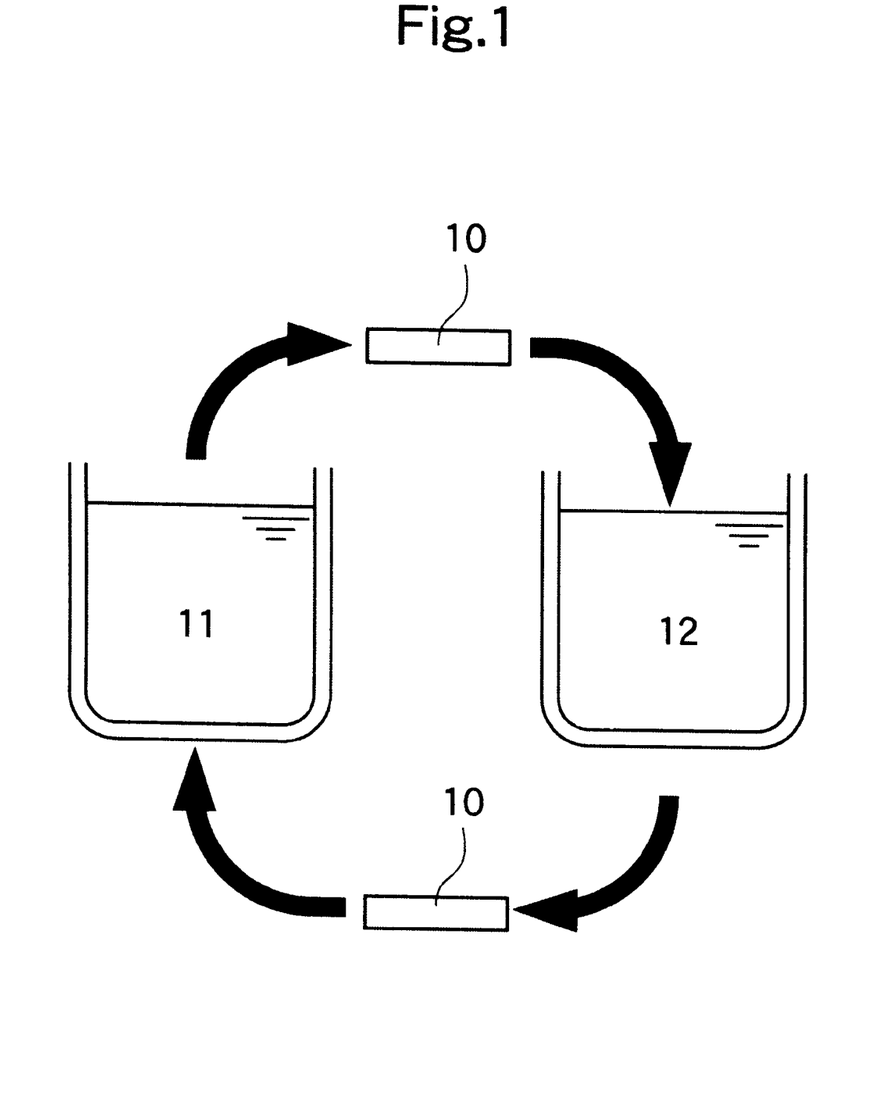
FIG. 1 is a scheme illustrating the steps in Example 1 in which a polyvinyl alcohol (abbreviated hereinbelow as PVA) gel is immersed in a calcium chloride solution and in a sodium hydrogenphosphate solution to produce HAp of the present invention.

Four sorts of PVA gel sample substrates obtained in the Synthesis Example 1 were each immersed in 10 ml of a 200 mM $CaCl_2$/Tris-HCl aqueous solution (pH7.4, liquid temperature of 37° C.) for 2 hours (this immersing operation in the solution containing calcium ions is referred to hereinbelow as "immersion (i)"). Subsequently, water was wiped with Kimwipe off the surface of the sample substrates. The wiped sample substrates were then immersed in 10 ml of a 120 mM $Na_2HPO_4$ aqueous solution (liquid temperature 37° C.) for 2 hours (this immersing operation in the solution containing phosphate ions is referred to hereinbelow as "immersion (ii)"). This alternate operation of the immersion (i) and immersion (ii) is referred to as one cycle. 1 to 15 cycles were performed, and the following observation, measurement and analysis were performed. Scheme of this alternate immersing operation is shown in FIG. 1. In FIG. 1, 10 is a sample substrate (PVA gel), 11 is a $CaCl_2$/Tris-HCl (pH 7.4, liquid temperature 37° C.) aqueous solution, and 12 is a $Na_2HPO_4$ aqueous solution (liquid temperature 37° C.).

Figure 2:
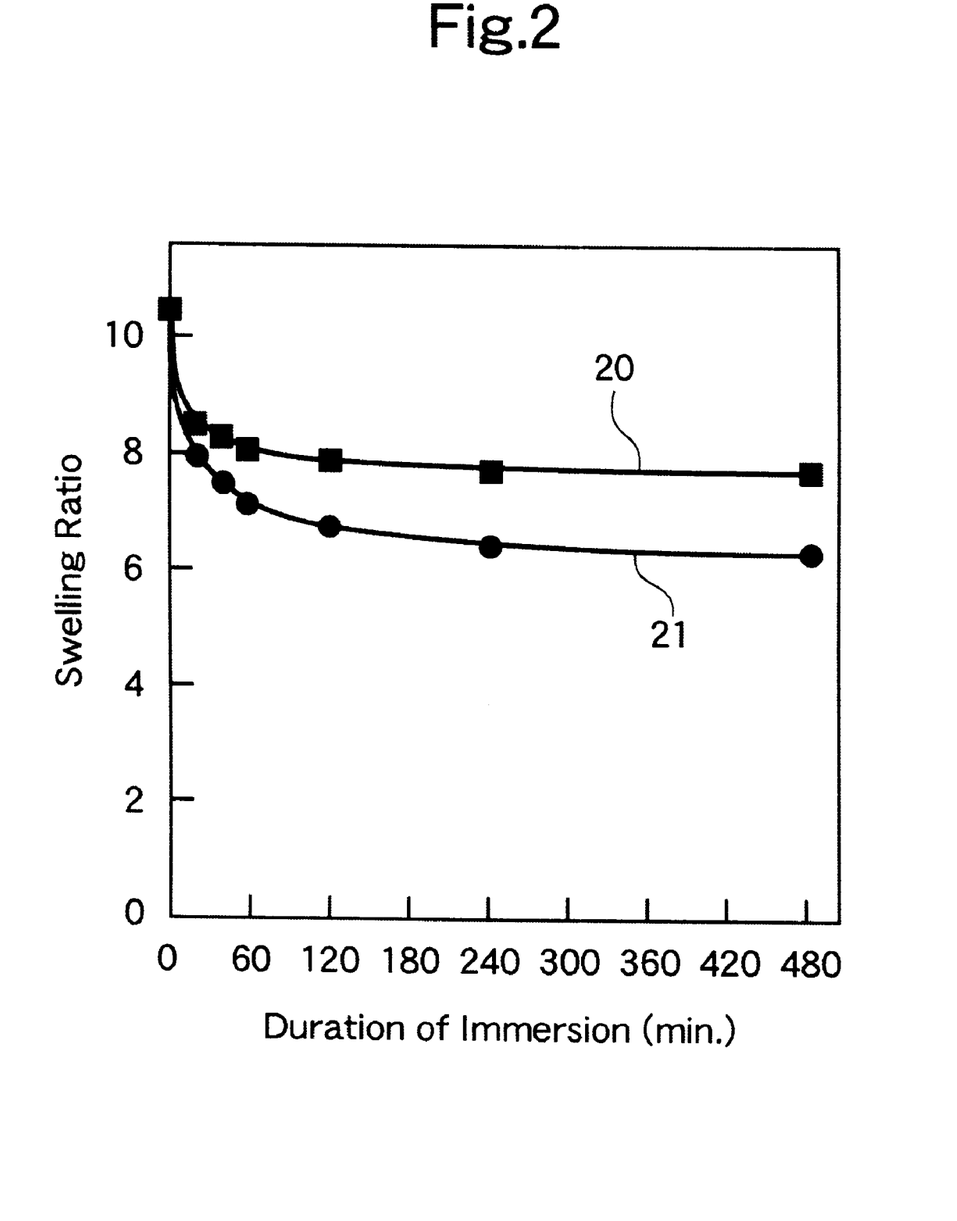
FIG. 2 is a graph showing a relation between time and swelling ratio as a result of immersion of the PVA gel in the calcium chloride solution and in the sodium hydrogenphosphate solution.

(1) Swelling ratio of the sample substrate PVA gel with respect to the duration of immersion (i) and immersion (ii) was measured. The results are shown in FIG. 2. In FIG. 2, 21 shows the relation between the duration of immersion (i) and swelling ratio, and 22 shows the relation between the duration of immersion (ii) and swelling ratio.

From the results in FIG. 2, it is seen that the swelling ratio of the PVA gel does not significantly change after about two hours from the beginning of the immersion (i) or (ii).

(2) X-ray diffraction analysis was performed for a HAp formed on a sample substrate after the alternate immersion of the sample substrate (PVA gel) having the swelling ratio 10.4. The results are shown in FIG. 3. In FIG. 3, 30 is the result of X-ray diffraction for the sample substrate before alternate immersion, 31 is the result of X-ray diffraction for HAp formed on the sample substrate after one cycle of the alternate immersing operation, and 32 is the result of X-ray diffraction for HAp formed on the sample substrate after 5 cycles of the alternate immersing operation. Those formed on the sample substrate by one or five cycles of alternate immersion were analyzed by EPMA (Electron Probe Micro Analysis) method with an apparatus Shimadzu EMX-SM (manufactured by Shimazu Co., Kyoto, Japan). As a result, it was found out that the composition thereof was substantially $Ca_{10}(PO_4)_6(OH)_2$.

From the results in FIG. 3, it is seen that both HAps generated by 1 or 5 cycles of alternate immersion have diffraction peaks at 31–32° and 26°, and that the peak intensity thereof increases as the number of cycles of the alternate immersion increases.

Figure 4A:
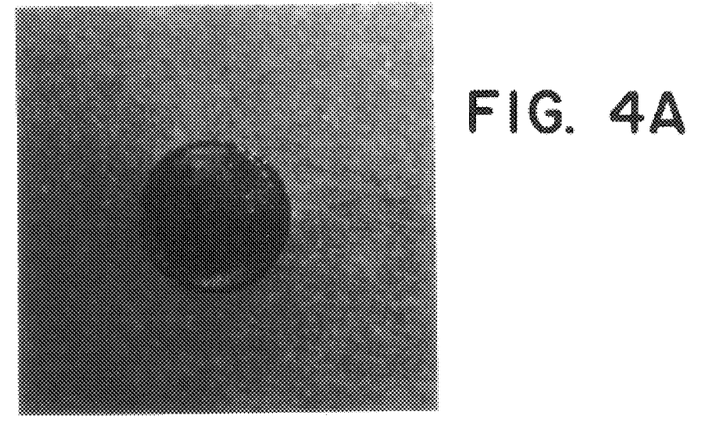
FIG. 4 is a set of microscopic photographs showing the formation of HAp of the present invention on the PVA gel. (a) is a photograph of the PVA gel, (b) is a photograph of the PVA gel after immersing the gel alternately in the calcium chloride solution and in the sodium hydrogenphosphate solution one time each, and (c) is a photograph of the PVA gel after immersing the gel alternately in the calcium chloride solution and the in sodium hydrogenphosphate solution five times each.
Figure 4B:
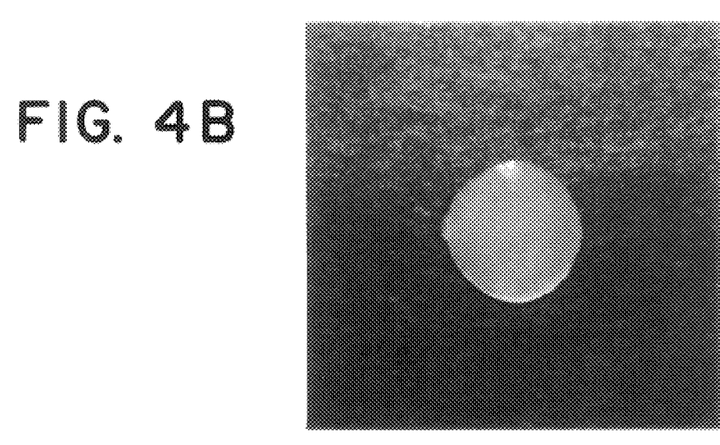
Figure 4C:
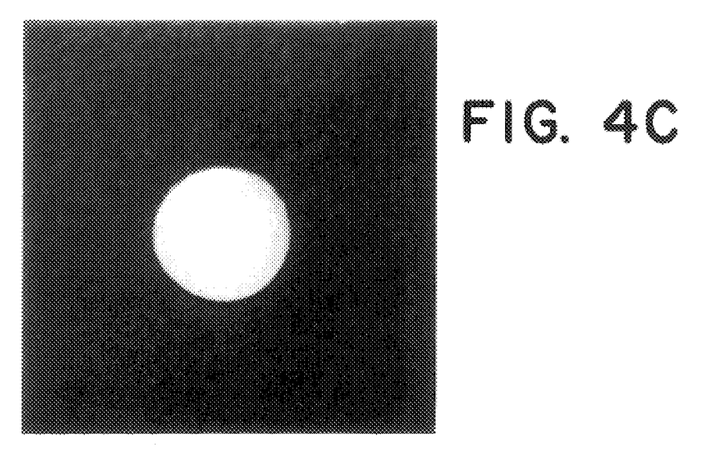
Figure 5A:
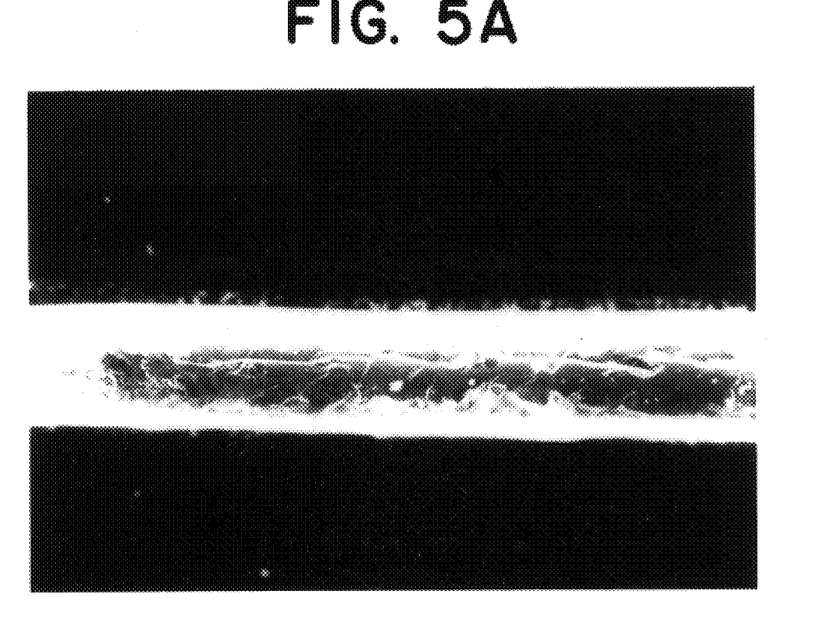
Figure 5B:
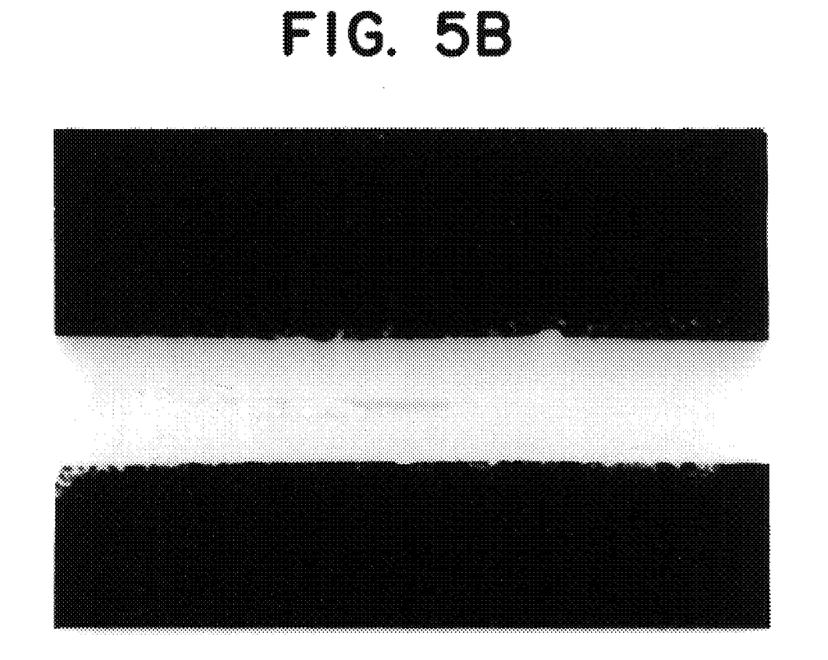
Figure 5C:
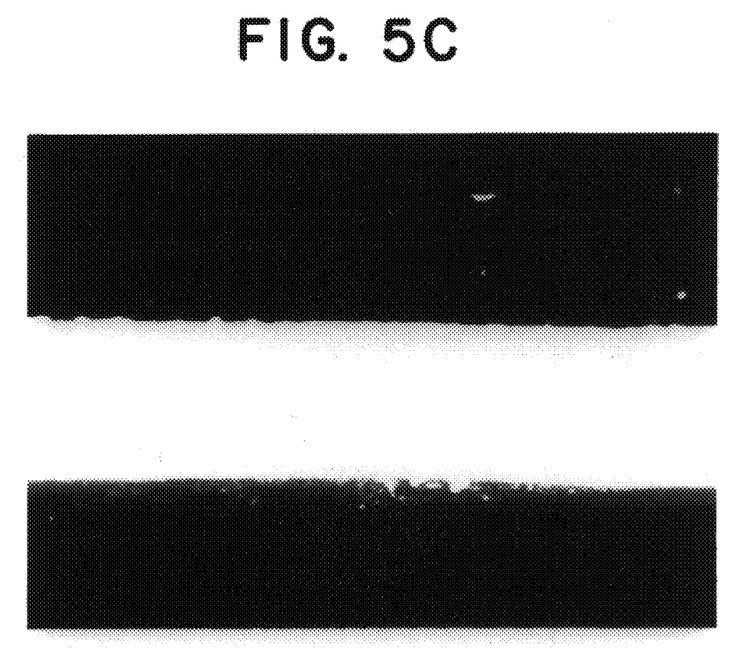
Figure 5D:
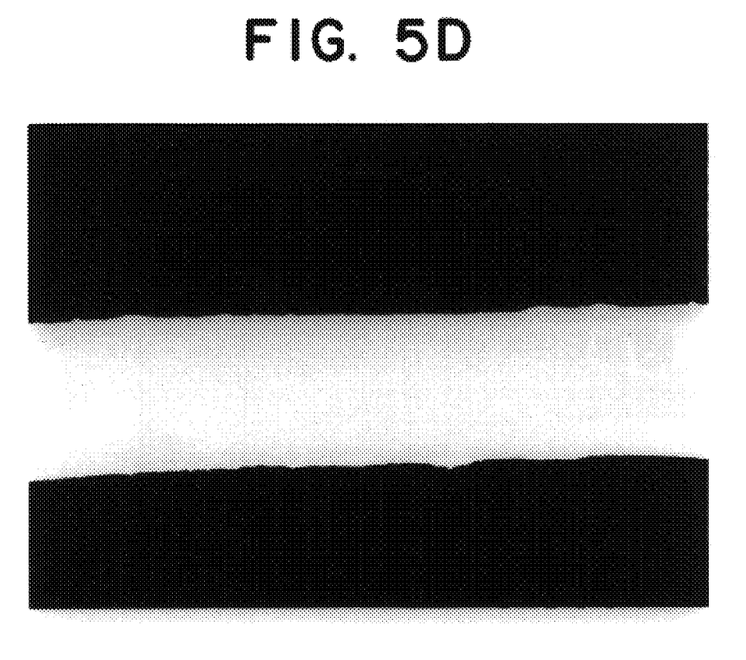

(3) Observations by taking photographs were performed for an HAp formed on the surface of the sample substrate (PVA gel) having a swelling ratio of 10.4 by the alternate immersion. The results are shown in FIG. 4. In FIG. 4, (a) is a photograph of the sample substrate (PVA gel), (b) is a photograph of the surface of the sample substrate after one cycle of the alternate immersion, and (c) is a photograph of the surface of the sample substrate after five cycles of the alternate immersion.

From the results in FIG. 4, it is seen that the sample substrate PVA gel becomes white as the number of cycles of the alternate immersion increases. In the photograph (c) taken after five cycles of the alternate immersion, slight shrinkage of the PVA gel of the sample substrate is observed.

(4) The state of the HAp formed inside the sample substrate (PVA gel) having a swelling ratio of 10.4 after the alternate immersion was observed by microscopic photographic observation of the cross-section of the sample substrate under the magnification of about 13. The results are shown in FIG. 5. In FIG. 5, (a) is a photograph of the cross-section of the sample substrate (PVA gel) after one cycle of the alternate immersing operation, (b) is a photograph of the cross-section of the sample substrate (PVA gel) after five cycles of the alternate immersing operation, (c) is a photograph of the cross-section of the sample substrate (PVA gel) after ten cycles of the alternate immersing operation, and (d) is a photograph of the cross-section of the sample substrate (PVA gel) after fifteen cycles of the alternate immersing operation.

It is seen from results in FIG. 5 that white crystals of HAp were formed on the surface of the sample substrate after one cycle of the alternate immersing operation, and that formation of the crystals progresses from the surface to inside of the sample substrate as the number of cycles of the alternate immersing operation increases up to 5, 10 or 15 cycles.

Figure 6:
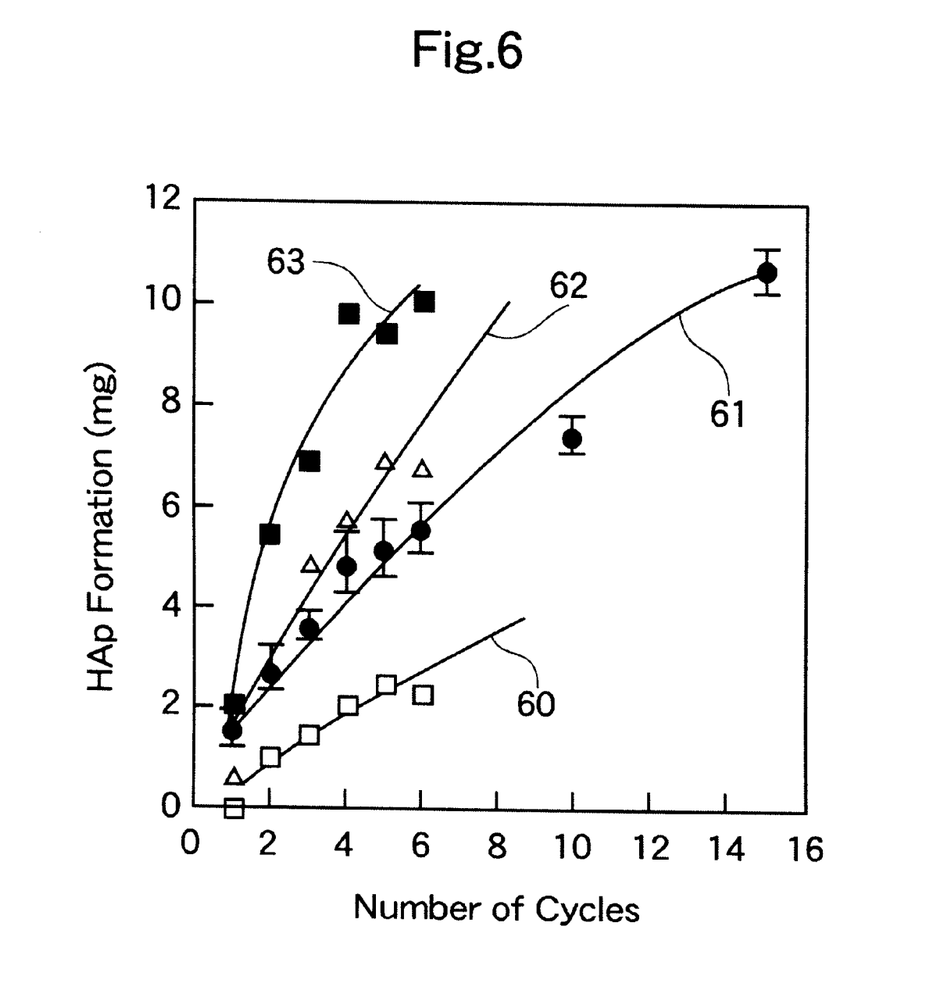
FIG. 6 is a graph showing the relation between the amount of HAp of the present invention formed on the PVA gel in each cycle and swelling ratio of the PVA gel, wherein one cycle is defined as a series of operations of immersing a PVA gel having a swelling ratio of 4 to 30 alternately in the calcium chloride solution and in the sodium hydrogenphosphate solution one time each.

(5) With four sorts of sample substrates each having a different swelling ratio, relation was determined between the amount of HAp formation on and/or in the sample substrate per cycle and swelling ratio of the sample substrate. The results are shown in FIG. 6. In FIG. 6, 60 is the result of the sample substrate having a swelling ratio of 4.1, 61 is the result of the sample substrate having a swelling ratio of 10.4, 62 is the result of the sample substrate having a swelling ratio of 16.8, and 63 is the result of the sample substrate having a swelling ratio of 30.1.

The relation between the swelling ratio of the four substrates and the amount of HAp formed on and/or in each sample substrate after a certain cycles of immersing operation is plotted. The result is shown in FIG. 7.

Figure 8:
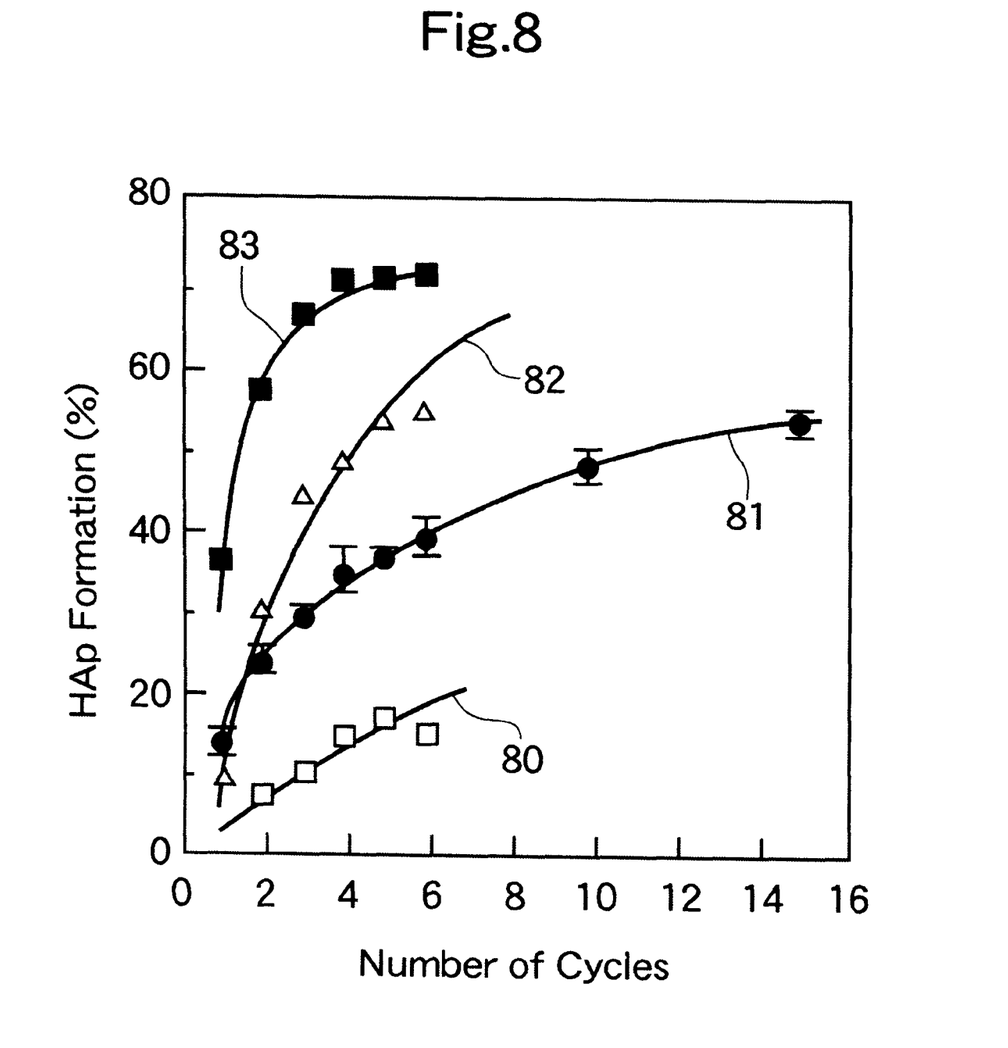
FIG. 8 is a graph showing the relation between the number of cycles for the PVA gel at each swelling ratio and the ratio of the formed HAp of the present invention on and/or in the PVA gel, wherein one cycle is defined as a series of operations of immersing a PVA gel alternately in the calcium chloride solution and in the sodium hydrogenphosphate solution one time each.

Further, the relations between the ratio of the formed HAp on and/or in the sample substrates having various swelling ratio and the number of cycles were plotted. The results are shown in FIG. 8. In FIG. 8, 80 is the result of the sample substrate having a swelling ratio of 4.1, 81 is the result of the sample substrate having a swelling ratio of 10.4, 82 is the result of the sample substrate having a swelling ratio of 16.8, and 83 the result of the sample substrate having a swelling ratio of 30.1.

Figure 7:
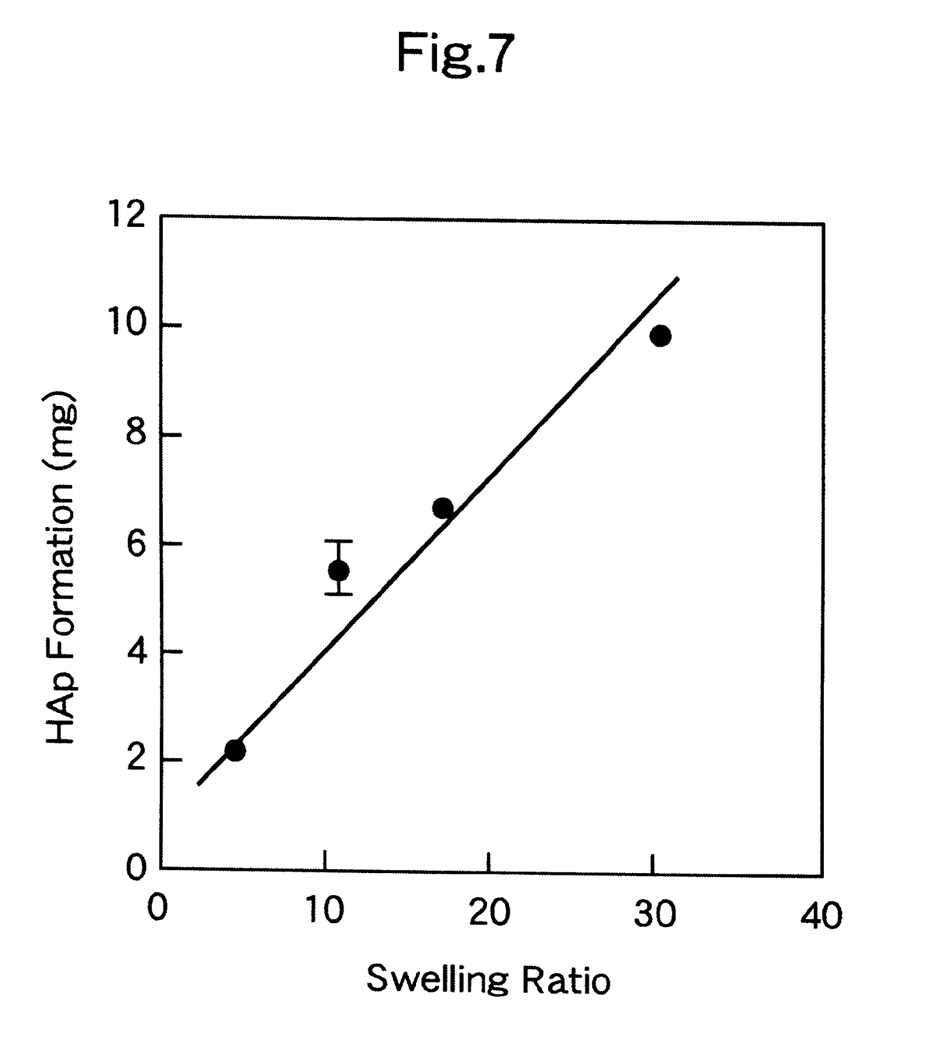
FIG. 7 is a graph showing the relation between the swelling ratio of the PVA gel and the amount of HAp of the present invention formed on and/or in the PVA gel after certain cycles of immersing operation, wherein one cycle is defined as a series of operations of immersing a PVA gel alternately in the calcium chloride solution and in the sodium hydrogenphosphate solution one time each.

From the results in FIGS. 6 to 8, it is seen that a sample substrate having higher swelling ratio tends to give a larger amount and ratio of HAp formation, and that production efficiency of HAp can be controlled in a degree by selecting the immersion time and the number of cycles. Further, it is seen that, with the sample substrate having a swelling ratio of 16.8, about 8 mg of HAp has been produced after the sixth cycle, that is, 24 hours from the beginning of the immersion. Comparing this result with the aforementioned result in Comparative Example 1, HAp production rate in the method of this Example is 100 times faster than the prior art biomimetic process.

What is claimed is:

1. A method for producing a hydroxyapatite consisting essentially of $Ca_{10}(PO_4)_6(OH)_2$ and having a crystal structure that causes diffraction peaks at 31–32° and 26° in X-ray diffractometry comprising the steps of:

(A) immersing a substrate in a first aqueous solution which contains calcium ions and is substantially free of phosphate ions and in a second solution which contains phosphate ions and is substantially free of calcium ions, to produce the hydroxyapatite at least on a surface of the substrate; and (B) recovering the hydroxyapatite from the substrate.

2. A method for producing a complex comprising a substrate and a hydroxyapatite consisting essentially of $Ca_{10}(PO_4)_6(OH)_2$, and having a crystal structure that causes diffraction peaks at 31–32° and 26° in X-ray diffractometry at least on a surface of said substrate comprising the step of immersing a substrate in a first aqueous solution which contains calcium ions and is substantially free of phosphate ions and in a second solution which contains phosphate ions and is substantially free of calcium ions, to produce the hydroxyapatite at least on a surface of the substrate.

3. A method for manufacturing a medical material, which comprises:

(A) immersing a substrate in a first aqueous solution which contains calcium ions and is substantially free of phosphate ions and in a second solution which contains phosphate ions and is substantially free of calcium ions, to produce a hydroxyapatite consisting essentially of $Ca_{10}(PO_4)_6(OH)_2$, and having a crystal structure that causes diffraction peaks at 31–32° and 26° in X-ray diffractometry at least on the surface of the substrate;

(B) recovering the hydroxyapatite from the substrate; and (C) manufacturing a medical material using the hydroxyapatite formed.

4. A method for manufacturing a medical material, which comprises:

(A) immersing a substrate in a first aqueous solution which contains calcium ions and is substantially free of phosphate ions and in a second solution which contains phosphate ions and is substantially free of calcium ions, to produce a complex having a hydroxyapatite consisting essentially of $Ca_{10}(PO_4)_6(OH)_2$, and having a crystal structure that causes diffraction peaks at 31–32° and 26° in X-ray diffractometry at least on the surface of the substrate; and (B) manufacturing a medical material using the complex formed.

* * * * *